(12) United States Patent
Wang et al.

(10) Patent No.: US 10,018,599 B2
(45) Date of Patent: Jul. 10, 2018

(54) CAPACITIVE TRANSDUCER AND METHOD OF MANUFACTURING THE SAME

(71) Applicant: CANON KABUSHIKI KAISHA, Tokyo (JP)

(72) Inventors: Shinan Wang, Komae (JP); Shinichiro Watanabe, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 157 days.

(21) Appl. No.: 14/562,955

(22) Filed: Dec. 8, 2014

(65) Prior Publication Data
US 2015/0183634 A1 Jul. 2, 2015

(30) Foreign Application Priority Data

Dec. 28, 2013 (JP) .................. 2013-273672

(51) Int. Cl.
| | | |
|---|---|---|
| B81B 3/00 | (2006.01) |
| B06B 1/02 | (2006.01) |
| B81C 1/00 | (2006.01) |
| G01N 29/24 | (2006.01) |
| G01N 29/44 | (2006.01) |

(Continued)

(52) U.S. Cl.
CPC ....... *G01N 29/2418* (2013.01); *B06B 1/0292* (2013.01); *B81B 7/0006* (2013.01); *G01N 29/0654* (2013.01); *G01N 29/2406* (2013.01); *B81B 2201/0271* (2013.01); *B81B 2203/0127* (2013.01); *B81B 2203/04* (2013.01); *B81B 2207/07* (2013.01)

(58) Field of Classification Search
CPC ................ B06B 1/0292; B81B 7/0006; B81B 2201/0271; B81B 2207/07; B81B 2203/04; B81B 2203/0127; B81B 3/0086; B81B 1/0292; B81C 1/0019; G01N 29/0654; G01N 29/2418; G01N 29/2406; G01N 29/44; G01N 2291/028
See application file for complete search history.

(56) References Cited

U.S. PATENT DOCUMENTS

| 6,836,020 B2 | 12/2004 | Cheng et al. |
| 2007/0180916 A1 | 8/2007 | Tian et al. |

(Continued)

FOREIGN PATENT DOCUMENTS

| JP | 2007-215177 A | 8/2007 | |
| JP | 2012-99518 A | 5/2012 | |
| JP | 2015128271 A | * 7/2015 | ........... B06B 1/0292 |

*Primary Examiner* — Daniel Pihulic
(74) *Attorney, Agent, or Firm* — Fitzpatrick, Cella, Harper & Scinto (57) ABSTRACT

The present inventions provide a capacitive transducer that can reduce film damage on a substrate surface on a vibration film side due to a difference in thermal expansion coefficient between a through wiring and a substrate and a method of manufacturing the same. The capacitive transducer consists of a plurality of cells with each cell comprising a first electrode and a vibration film on a first surface side of a substrate having a through wiring that penetrates the substrate from a first surface to a second surface of the substrate, the vibration film including a second electrode that is formed with a gap from the first electrode. A holding member that holds a leading end of the through wiring is provided on the first surface side of the substrate.

23 Claims, 3 Drawing Sheets

(51) Int. Cl.
*G01N 29/06* (2006.01)
*B81B 7/00* (2006.01)

(56) References Cited

U.S. PATENT DOCUMENTS

2015/0183634 A1* 7/2015 Wang .................... B06B 1/0292
73/643
2015/0290679 A1* 10/2015 Kandori ................ B06B 1/0292
367/7

* cited by examiner

CAPACITIVE TRANSDUCER AND METHOD OF MANUFACTURING THE SAME

BACKGROUND OF THE INVENTION

Field of the Invention

The present invention relates to a capacitive transducer used as an ultrasonic conversion element and a method of manufacturing the capacitive transducer.

Description of the Related Art

Up to now, a capacitive transducer (capacitive micromachined ultrasonic transducer (CMUT)) manufactured using micromachining technology has been studied as an alternative to a piezoelectric element. The CMUT can transmit and receive acoustic waves by means of vibrations of a vibration film, and can be easily provided with excellent broadband characteristics particularly in liquid. Note that, herein, the acoustic waves include waves called sonic waves, ultrasonic waves and photoacoustic waves. For example, the acoustic waves include photoacoustic waves that are generated inside of a subject by irradiating the inside of the subject with light (electromagnetic waves) such as visible light and infrared light. In actual use, a plurality of vibration films placed in a two-dimensional array is defined as one element, and a plurality of the elements is further arranged on a substrate, whereby a transducer is configured so as to achieve desired performance. In order to independently control each element, wiring electrodes respectively corresponding to the elements need to be formed. In this case, in order to reduce a structure size and the parasitic capacitance of each wiring electrode, it is desirable to use a through wiring that passes through the substrate. Meanwhile, in the case where the material of the through wiring is different from the material of the substrate, an end part of the through wiring may protrude from the substrate surface to deform or break through thin films located above the end part of the through wiring, due to a difference in thermal expansion coefficient in a high-temperature process after the formation of the through wiring.

U.S. Pat. No. 6836020 discloses a CMUT including a substrate made of silicon and a through wiring made of polycrystalline silicon. In this configuration, the through wiring made of polycrystalline silicon and the substrate made of silicon have approximately similar thermal expansion coefficient as each other, and hence a change in position of an end part of the through wiring relative to the substrate surface is small even at high temperature. Moreover, Japanese Patent Application Laid-Open No. 2007-215177 discloses a CMUT in which a glass substrate having a through wiring formed therein and another substrate are joined to each other. In this configuration, when thin films including a vibration film are formed on the other substrate, the thin films are not influenced by the through wiring. Moreover, Japanese Patent Application Laid-Open No. 2012-99518 discloses a through wiring structure configured using a concave part and a plurality of fine holes formed on the bottom surface of the concave part. In this two-stage wiring configuration, because the fine holes are small, a stress applied to thin films located above an end part of the through wiring is small even at high temperature.

However, in the case of the through wiring made of polycrystalline silicon in U.S. Pat. No. 6836020, because the resistivity of the polycrystalline silicon is high, it is far from easy to reduce the resistance of the through wiring. In the case of the joining method in Japanese Patent Application Laid-Open No. 2007-215177, a lower electrode is directly connected to an end part of the through wiring, and hence deformation of the lower electrode due to thermal deformation of the through wiring is unavoidable. Furthermore, in the case of the two-stage wiring configuration in Japanese Patent Application Laid-Open No. 2012-99518, the number of manufacturing steps is large, and a substrate area occupied by the through wiring is large. Hence, this configuration is not suitable for a reduction in size.

SUMMARY OF THE INVENTION

In view of the above-mentioned problems, the present invention provides a method of manufacturing a capacitive transducer having a cell comprising a first electrode and a vibration film on a first surface side of a substrate having a through wiring that passes through the substrate between a first surface and a second surface of the substrate, the vibration film including a second electrode that is formed with a gap from the first electrode. The method comprises: forming a holding member that holds a leading end of the through wiring, on the first surface side of the substrate having the through wiring; and forming the cell after forming the holding member.

Moreover, in view of the above-mentioned problems, the present invention provides a capacitive transducer having a cell comprising a first electrode and a vibration film on a first surface side of a substrate having a through wiring that passes through the substrate between a first surface and a second surface of the substrate, the vibration film including a second electrode that is formed with a gap from the first electrode. A holding member that holds a leading end of the through wiring is provided on the first surface side of the substrate.

Further features of the present invention will become apparent from the following description of exemplary embodiments with reference to the attached drawings.

DESCRIPTION OF THE EMBODIMENTS

In the present invention, a holding member that holds a leading end of a through wiring is formed on a first surface side of a substrate having the through wiring. Hence, when a thin film CMUT is manufactured on the substrate having the through wiring, film damage due to a difference in thermal expansion coefficient between the through wiring and the substrate can be reduced.

Preferred embodiments of the present invention will now be described in detail in accordance with the accompanying drawings.

First Embodiment

Figure 1A:
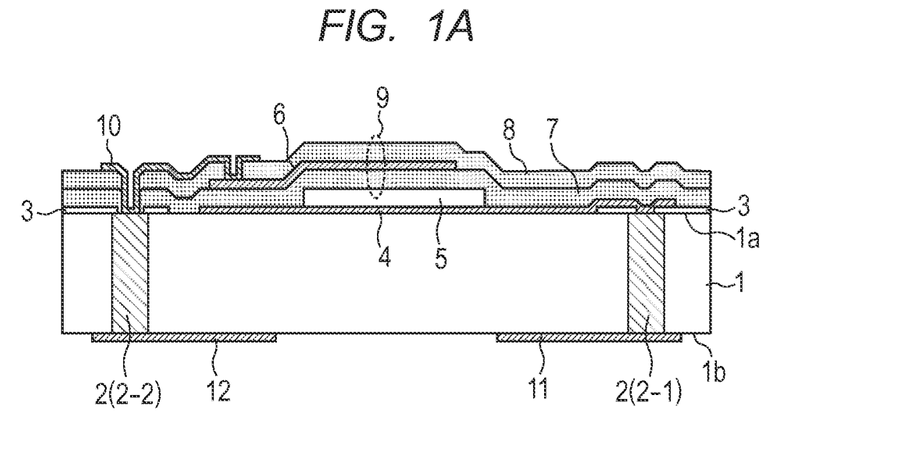
FIG. 1A and FIG. 1B are diagrams for describing an example capacitive transducer according to the present invention.
Figure 1B:
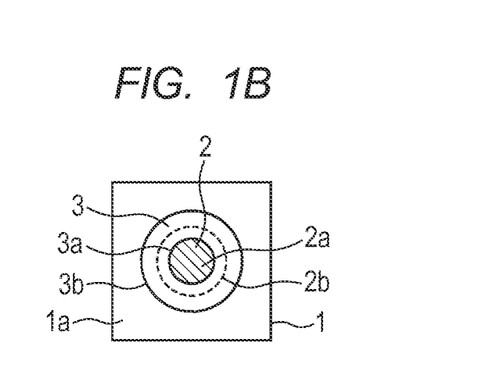

With reference to FIG. 1A and FIG. 1B, a basic configuration of a first embodiment of a capacitive transducer of the present invention is described. FIG. 1A is a cross-sectional view of the capacitive transducer, and FIG. 1B is a plan view illustrating example shapes of a holding member and a leading end of a through wiring and an example positional relation therebetween. For the sake of simplicity, only one cell (one vibration film) of the capacitive transducer is illustrated in FIG. 1A.

As illustrated in FIG. 1A, the capacitive transducer of the present embodiment includes: a substrate 1 having a first surface 1a and a second surface 1b; and through wirings 2 (including 2-1 and 2-2) that pass through the substrate 1 between the first surface 1a and the second surface 1b that is opposed to each other. Moreover, the capacitive transducer of the present embodiment has a cell structure in which a vibration film 9 that can be vibrate is supported, the vibration film 9 including: a second electrode 6 that is provided with a gap 5 from a first electrode 4 formed on the first surface side of the substrate 1; and insulating films 7 and 8 that are respectively formed on lower and upper sides of the second electrode 6. Then, a holding member 3 that holds a leading end of each through wiring 2 is formed on the first surface 1a side of the substrate 1. The substrate 1 is selected so as to suit the performance of the capacitive transducer. For example, the substrate 1 is made of an insulating material such as glass. Alternatively, the substrate 1 may be made of any of high-resistance silicon and low-resistance silicon. The thickness of the substrate 1 is, for example, 100 µm to 1,000 µm.

Each through wiring 2 is made of a low-resistivity material. For example, the through wiring 2 is made of a material containing metal. Desirably, the through wiring 2 has a low-resistance structure containing Cu as a main material thereof. The cross-sectional shape of the through wiring 2 observed in a direction perpendicular to the first surface 1a of the substrate 1 is designed in consideration of the capacitance and the resistance of the through wiring 2 and the easiness in manufacturing the through wiring 2. The cross-sectional shape of the through wiring 2 may be uniform or non-uniform in the length direction thereof. As an example, the cross-sectional shape of the through wiring 2 is substantially circular, and the diameter thereof is 20 µm to 100 µm.

The holding member 3 for each through wiring 2 is formed on the first surface 1a side of the substrate 1 so as to hold the leading end of the through wiring 2. The holding member 3 has: a portion that closely adheres to the first surface 1a of the substrate 1; a portion for holding part of the leading end of the through wiring 2; and an opening for exposing part of the leading end of the through wiring 2. The holding member 3 is designed to have both features of the function of holding the leading end of the through wiring 2 and the opening for enabling connection between the through wiring 2 and one of the first electrode 4 and the second electrode 6. In particular, the holding member 3 is designed such that deformation of the first electrode 4 and the vibration film 9 due to maximum thermal deformation of the leading end of the through wiring 2 on the first surface 1a side of the substrate 1 does not influence the performance of the capacitive transducer. It is desirable that the holding member 3 be made of a material having a high Young's modulus. The holding member 3 may be a single-layer film or a multi-layer film.

The strength of the holding member 3 is determined depending on the material, the shape and the thickness thereof. For example, the holding member 3 is designed such that the yield stress thereof in the length direction of the through wiring 2 is equal to or more than 1.7 times the shear strength of the through wiring 2. Under this condition, when the through wiring 2 thermally deforms, the through wiring 2 starts to slide in a direction opposite to the holding member 3 before significantly deforming the holding member 3. As a result, even if the through wiring 2 deforms relative to the substrate 1 due to a difference in thermal expansion coefficient between the substrate 1 and the through wiring 2 at high temperature, the maximum stress that is applied by the through wiring 2 to thin films on the upper surface of the holding member 3 is suppressed. Accordingly, the thin films on the upper surface of the holding member 3 can be prevented from significantly deforming and breaking. In consideration of thermal deformation of the holding member 3 itself, it is desirable that the holding member 3 have a thermal expansion coefficient closer to the thermal expansion coefficient of the substrate 1 than the thermal expansion coefficient of the through wiring 2. For examples, the material of the holding member 3 may be any of silicon compounds such as silicon oxide and silicon nitride, titanium oxide (for example, $TiO_2$), yttrium oxide (for example, $Y_2O_3$) and aluminum oxide (for example, $Al_2O_3$). The thickness of the holding member 3 is, for example, 0.1 µm to 2 µm.

FIG. 1B illustrates example shapes of the holding member and the leading end of the through wiring and an example positional relation therebetween. In FIG. 1B, the holding member 3 is a circular plate with an opening having an inner circumference 3a and an outer circumference 3b, and is substantially concentric with the leading end of the through wiring 2 having a circular outer circumference 2b. In the region between the outer circumference 3b and the outer circumference 2b, the holding member 3 closely adheres to the first surface 1a of the substrate 1. In the region between the outer circumference 2b and the inner circumference 3a, the holding member 3 holds part of the leading end of the through wiring 2. In the region on the inner side of the inner circumference 3a, the holding member 3 has the opening, and a part 2a of the leading end of the through wiring 2 is exposed. As a more specific example, the inner circumference 3a of the holding member 3 is a circle having a diameter of 10 µm to 50 µm, and the distance between the inner circumference 3a of the holding member 3 and the outer circumference 2b of the leading end of the through wiring 2 is 5 µm to 50 µm. Moreover, the distance between the outer circumference 3b of the holding member 3 and the outer circumference 2b of the leading end of the through wiring 2 is 5 µm to 500 µm.

The holding member 3 may be rotationally symmetric or may not be rotationally symmetric. Moreover, the holding member 3 may not be placed concentrically with the leading end of the through wiring 2. Moreover, the holding member 3 may be formed in direct contact with the first surface 1a of the substrate 1, or may be formed on the first surface 1a side of the substrate 1 with the intermediation of a film that closely adheres to the first surface 1a of the substrate 1.

The first electrode 4 is formed on the first surface 1a side of the substrate 1. In the case where the substrate 1 has insulation properties, the first electrode 4 may be formed directly on the surface of the substrate 1. Moreover, for the purpose of improving close adhesiveness and electrical insulation properties, the first electrode 4 may be formed on the first surface 1a side of the substrate 1 with the intermediation of a film that closely adheres to the first surface 1a of the substrate 1. The first electrode 4 is connected to the through wiring 2-1 that is one of the through wirings 2, and is further connected to an electrode pad 11 formed on the second surface 1b side of the substrate 1 through the through wiring 2-1.

The second electrode 6 is provided on the first surface 1a side of the substrate 1 with the gap 5. For electrical insulation, the second electrode 6 is formed so as to be sandwiched between the insulating films 7 and 8. The second electrode 6 is connected to the through wiring 2-2 that is one of the through wirings 2 by a wiring electrode 10, and is further connected to an electrode pad 12 formed on the second surface 1b side of the substrate 1 through the through wiring 2-2. The wiring electrode 10 has a portion connected to the leading end of the through wiring 2-2, and at least part of the outer circumference of the connected portion is located on the inner side of the opening of the holding member 3. More desirably, the connected portion is located completely on the inner side of the opening of the holding member 3. With this configuration, even if film deformation occurs near the opening of the holding member 3, the second electrode 6 and the leading end of the through wiring 2-2 are reliably electrically connected to each other regardless of the deformation. Both of the first electrode 4 and the second electrode 6 may not be electrically drawn out to the second surface 1b side of the substrate 1 through the through wirings 2, and only any one thereof may be drawn out to the second surface 1b side therethrough.

The area and the height (thickness) of the gap 5 are designed depending on the performance of the capacitive transducer. When the capacitive transducer is driven, the gap 5 deforms while following vibrations of the vibration film 9. As an example, the gap 5 has a structure close to a column having a diameter of 10 μm to 100 μm and a height of 50 nm to 500 nm.

The insulating films 7 and 8 not only serve as insulating protective films for the second electrode 6 but also form the vibration film 9 of the cell together with the second electrode 6. The material and the film thickness of each of the insulating films 7 and 8 are designed depending on required performance and specifications of the capacitive transducer. As an example, the insulating films 7 and 8 are made of silicon nitride, and each have a thickness of 100 μm to 1,000 μm. As a matter of course, the insulating films 7 and 8 may be made of materials different from each other. Moreover, the insulating films 7 and 8 may be single-layer films or multi-layer films.

It is desirable that the vibration film 9 including the insulating film 7, the second electrode 6 and the insulating film 8 have a tensile stress of 1 GPa or less. In the case where the vibration film 9 has a compressive stress, one of sticking and buckling may occur in the vibration film 9, so that the vibration film 9 may significantly deform. The sticking in this case means that the vibration film 9 sticks to the first electrode 4 on the substrate 1 side. On the other hand, in the case where the vibration film 9 has an excessively high tensile stress, the vibration film 9 is likely to break. The material, the film thickness, film formation conditions and heat treatment conditions of each of the insulating film 7, the second electrode 6 and the insulating film 8 are designed such that the vibration film 9 has a tensile stress of 1 GPa or less. Moreover, for the purpose of improving close adhesiveness between films and insulation properties and preventing interdiffusion, films having such effects and functions may be respectively provided between adjacent films of the insulating film 7, the second electrode 6, the insulating film 8 and the wiring electrode 10.

Although not illustrated, the capacitive transducer is electrically connected to a control circuit with the intermediation of the electrode pads 11 and 12. Example methods used for this connection include connection using bumps, wire bonding, and connection using an anisotropic conductive film (ACF). When the capacitive transducer is driven, bias voltage is applied to the first electrode 4, and the second electrode 6 is used as one of a signal application electrode and a signal take-out electrode. Alternatively, the opposite may be adopted.

As described above, in the capacitive transducer of the present embodiment, the leading end of each through wiring is held by the holding member, on the substrate surface side on which the vibration film is formed. Accordingly, even in a temperature rising state during manufacture, the end part of the through wiring is suppressed from protruding toward the holding member. As a result, even if the thermal expansion coefficient of the through wiring and that of the substrate are different from each other, damage of the vibration film and the lower electrode of the capacitive transducer due to thermal deformation of the through wiring can be prevented. Accordingly, the through wiring can be made of a metal material different from the substrate material, and the resistance of the through wiring can be remarkably reduced. Moreover, the electrode and the through wiring can be reliably connected to each other. In this way, the through wiring can be made of a low-resistivity metal material, whereby the resistance of the through wiring can be remarkably reduced. If the through wiring is made of such a low-resistivity metal material, even if the through wiring is thinned, a sufficiently low wiring resistance can be obtained. If the through wiring is thinned, a substrate area occupied by the through wiring can be made smaller, and the size of the capacitive transducer can be reduced.

Second Embodiment

Figure 2A:
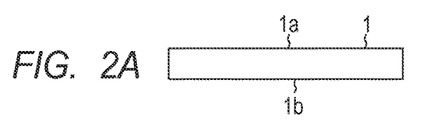
FIG. 2A, FIG. 2B, FIG. 2C, FIG. 2D, FIG. 2E, FIG. 2F, FIG. 2G, FIG. 2H, FIG. 2I, FIG. 2J, FIG. 2K, FIG. 2L, FIG. 2M, FIG. 2N, FIG. 2O, FIG. 2P and FIG. 2Q are diagrams for describing an example method of manufacturing a capacitive transducer according to the present invention.

A second embodiment related to a method of manufacturing a capacitive transducer of the present invention is described. FIG. 2A to FIG. 2Q are cross-sectional views for describing the manufacturing method of the present embodiment. For the sake of simplicity, only one cell (one vibration film) of the capacitive transducer is illustrated in FIG. 2A to FIG. 2Q.

First, as illustrated in FIG. 2A, the substrate 1 having the first surface 1a and the second surface 1b opposed to each other is prepared. The substrate 1 is selected so as to suit the performance of the capacitive transducer. For example, the substrate 1 is made of an insulating material such as glass. Alternatively, the substrate 1 may be made of any of high-resistance silicon and low-resistance silicon. In the present embodiment, the substrate 1 made of low-resistance silicon is taken as an example. The thickness of the substrate 1 is, for example, 100 μm to 1,000 μm. In order to reduce variation in performance among cells, it is desirable that the first surface 1a of the substrate 1 be flat and smooth. For example, a surface roughness Ra of the first surface 1a of the substrate 1 is less than 10 nm.

Figure 2B:
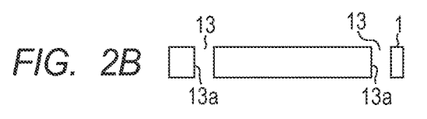

Then, as illustrated in FIG. 2B, through holes 13 are formed penetrating the substrate 1 from the first surface 1a to the second surface 1b, and the first surface 1a and the second surface 1b are opposed to each other. Each through hole 13 functions as a hole for inserting a predetermined through electrode (through wiring) 2. The cross-sectional shape of the through hole 13 may be uniform or non-uniform in the length direction thereof. As an example, the through hole 13 has a substantially columnar shape having a diameter of 20 μm to 100 μm. The through hole 13 is formed using, for example, a deep reactive ion etching (RIE) technique of silicon. The substrate 1 is processed using RIE from both sides of the first surface 1a and the second surface 1b if needed. Moreover, if needed, an inner wall 13a of the through hole 13 is smoothed such that a surface roughness Rmax of the inner wall 13a becomes less than 100 nm.

Figure 2C:
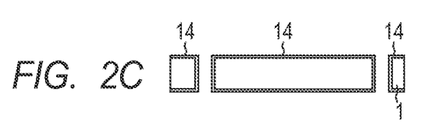

Then, as illustrated in FIG. 2C, an insulating film 14 is formed on the surface of the substrate 1 including the first surface 1a, the second surface 1b and the inner wall 13a of each through hole 13 (see FIG. 2B). The insulating film 14 is made of, for example, any of silicon oxide, silicon nitride and aluminum oxide ($Al_2O_3$), and a material having high insulation properties is desirably used therefor. The thickness of the insulating film 14 is determined by required dielectric strength voltage and material characteristics. The thickness of the insulating film 14 is, for example, 0.1 μm to 2 μm. For example, the methods of forming the insulating film 14 include thermal oxidation, chemical vapor deposition (CVD), and atomic layer deposition (ALD). The insulating film 14 may be a single-layer film or a multi-layer film. Moreover, if needed, a close adhesion layer may be formed between the surface of the substrate 1 and the insulating film 14.

Figure 2D:
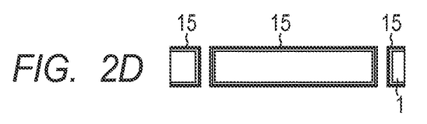

Then, as illustrated in FIG. 2D, an insulating film 15 is further formed on the surface of the insulating film 14. One of roles of the insulating film 15 having insulation properties is to serve as a barrier layer for preventing the material of the through wirings 2 to be formed in FIG. 2E from diffusing to the insulating film 14. The insulating film 15 is made of, for example, any of silicon nitride and titanium nitride. The thickness of the insulating film 15 is, for example, 0.01 μm to 0.5 μm. The insulating film 15 is formed using, for example, the CVD method.

Figure 2E:
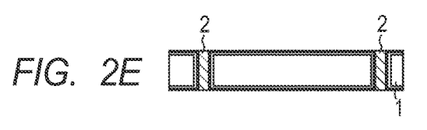

Then, as illustrated in FIG. 2E, the through wirings 2 that penetrate the substrate 1 from the first surface 1a to the second surface 1b, the first surface 1a and he second surface 1b are opposed to each other, are respectively formed in the through holes 13 (see FIG. 2B). Each through wiring 2 is made of a low-resistivity material. Desirably, the through wiring 2 is made of a material containing metal. For example, the through wiring 2 has a structure containing Cu as a main material thereof. The through wiring 2 is formed so as to substantially fill the inside of the through hole 13. Example methods of forming the through wiring 2 include plating. In particular, a method in which electrolytic plating is performed with one surface of the substrate 1 (for example, the second surface 1b of the substrate 1) closely adhering to a substrate with a seed layer can be adopted. After the plating, the substrate with the seed layer is separated from the substrate 1. Then, the first surface 1a and the second surface 1b of the substrate 1 are planarized by polishing. Chemical mechanical polish (CMP) is preferable as the polishing method. The surface roughness Ra of the first surface 1a of the substrate 1 is made less than 10 nm by performing CMP. For example, in the case where the through wiring 2 contains Cu as the main material thereof, after the plating, the end surfaces of the through wiring 2 and the surfaces 1a and 1b of the substrate 1 are polished into substantially the same height (level) by performing CMP of Cu. In this case, the insulating film 15 (made of, for example, silicon nitride) serves as a stopper layer for the CMP of Cu. Then, if needed, the surface roughness of the first surface 1a of the substrate 1 is reduced by performing CMP on the insulating film 15.

In FIG. 2E, seemingly, two through wirings 2 are formed for one vibration film (one cell). In actual use, two through wirings 2 may be formed for a plurality of vibration films. For example, two through wirings 2 are formed for one element including a plurality of vibration films. The number of the through holes 13 corresponds to the number of the through wirings 2.

Figure 2F:
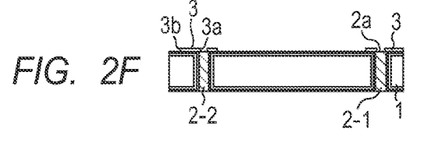

Then, as illustrated in FIG. 2F, the holding member 3 that holds the leading end of each through wiring 2 is formed on the first surface 1a side of the substrate 1. The holding member 3 includes: the portion that closely adheres to the first surface 1a of the substrate 1; the portion for holding part of the leading end of the through wiring 2; and the opening for exposing the part 2a of the leading end of the through wiring 2. The holding member 3 is designed such that deformation of the first electrode 4 and the vibration film 9 due to maximum thermal deformation of the leading end of the through wiring 2 in the subsequent heat treatment does not influence the performance of the cell. It is desirable that the holding member 3 be made of a material having a high Young's modulus. The holding member 3 may be a single-layer film or a multi-layer film. The strength of the holding member 3 is determined depending on the material, the shape and the thickness thereof. For example, the holding member 3 is formed such that the yield stress thereof in the length direction of the through wiring 2 is equal to or more than 1.7 times the shear strength of the through wiring 2. Moreover, in consideration of thermal deformation of the holding member 3, it is desirable that the holding member 3 have a thermal expansion coefficient closer to the thermal expansion coefficient of the substrate 1 than the thermal expansion coefficient of the through wiring 2.

For examples, the material of the holding member 3 include silicon oxide, silicon nitride, titanium oxide (for example, $TiO_2$), yttrium oxide (for example, $Y_2O_3$) and aluminum oxide (for example, $Al_2O_3$). The thickness of the holding member 3 is, for example, 0.1 μm to μm. The shape of the holding member 3 is, for example, a circular plate substantially concentric with the through wiring 2, as illustrated in FIG. 1B. The form of the holding member 3 is, for example, as described in the first embodiment. It is desirable that, when the holding member 3 is formed, relative deformation between the leading end of the through wiring 2 and the first surface 1a of the substrate 1 be as small as possible. Accordingly, it is desirable that the holding member 3 be formed at a temperature of 100° C. or lower. It is more desirable that the holding member 3 be formed at a temperature close to room temperature. A method of forming a film of the holding member 3 may be sputtering method. As a method of forming a pattern of the holding member 3, etching mask formation including photolithography, dry etching including reactive ion etching, or wet etching using chemicals can be used.

Figure 2G:
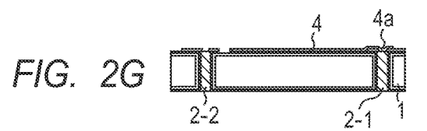

Then, as illustrated in FIG. 2G, the first electrode 4 is formed on the first surface 1a side of the substrate 1. The first electrode 4 is one of electrodes for driving the vibration film. The first electrode 4 is formed on the insulating film 14 and the insulating film 15, and hence being insulated from the substrate 1. The first electrode 4 includes: a portion located below a vibrating portion (a portion corresponding to the gap 5 in FIG. 20) of the vibration film 9 of the cell; and a portion 4a connected to the through wiring 2-1 that is one of the through wirings 2. The first electrode 4 is made of a material having high electrical conductivity. For example, the first electrode 4 is made of a film containing metal as a main component thereof. As an example, the first electrode 4 is made of a film containing Al as a main component thereof. The first electrode 4 may be comprised of a single-layer film or a multi-layer film. The first electrode 4 is electrically conductively formed for each cell in the same element. For example, as a method of forming the first electrode 4, a method including formation of a metal film, photolithography, dry etching and wet etching of the metal film can be used. The metal film is formed so as not to be disconnected around the holding member 3. A film forming method that gives excellent coating property, such as sputtering, is desirable to form the metal film.

Figure 2H:
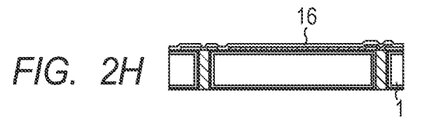

Then, as illustrated in FIG. 2H, an insulating film 16 is formed. The insulating film 16 covers the surface of the first electrode 4, and one of roles thereof is to serve as an insulating protective film for the first electrode 4. The insulating film 16 is made of, for example, any of silicon oxide, silicon nitride and aluminum oxide ($Al_2O_3$), and they desirably have high insulation properties. The thickness of the insulating film 16 is determined by required dielectric strength voltage and material characteristics, and for example, the thickness is 0.1 µm to 2 µm. It is desirable that the insulating film 16 be formed at a temperature of 400° C. or lower. For example, as a method of forming the insulating film 16, chemical vapor deposition, atomic layer deposition and sputtering can be used. The insulating film 16 may be a single-layer film or a multi-layer film. Moreover, if needed, a close adhesion layer may be formed under the insulating film 16.

Figure 2I:
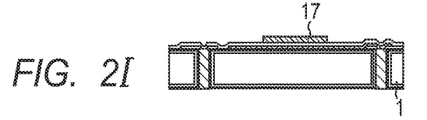

Then, as illustrated in FIG. 2I, a sacrifice layer 17 is formed. The sacrifice layer 17 serves to define the gap 5 (see FIG. 2N) of the cell, and is made of a material that can be selectively removed when the gap 5 is formed. The sacrifice layer 17 is made of, for example, one of a silicon-based material or metal such as Cr. As a method of forming a pattern of the sacrifice layer 17, a method including etching mask formation including photolithography, and dry etching including reactive ion etching or wet etching using chemicals can be used.

Figure 2J:
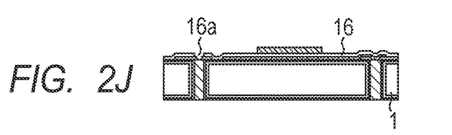

Then, as illustrated in FIG. 2J, a hole 16a is formed. The hole 16a is an opening of the insulating film 16, and serves to connect the second electrode 6 to the through wiring 2-2 that is one of the through wirings 2 (see FIG. 2Q). The hole 16a can preferably be slightly larger than the opening 3a of the holding member 3. As a method of forming the hole 16a, a method including etching mask formation including photolithography, and dry etching including reactive ion etching or wet etching using chemicals can be used.

Figure 2K:
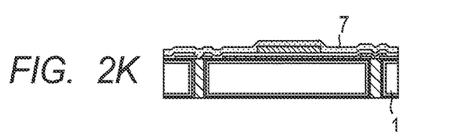

Then, as illustrated in FIG. 2K, the insulating film 7 is formed. The insulating film 7 spreads in contact with the entire lower surface of the second electrode 6 to be formed in FIG. 2L, and one of roles thereof is to serve as an insulating protective film for the second electrode 6. The insulating film 7 is made of, for example, any of silicon oxide, silicon nitride and aluminum oxide ($Al_2O_3$), and they desirably have high insulation properties. The thickness of the insulating film 7 is determined by required dielectric strength voltage and material characteristics, and for example, the thickness is 0.1 µm to 2 µm. It is desirable that the insulating film 7 be formed at a temperature of 400° C. or lower. For example, as a method of forming the insulating film 7, chemical vapor deposition, atomic layer deposition and sputtering can be used. The insulating film 7 may be a single-layer film or a multi-layer film.

Figure 2L:
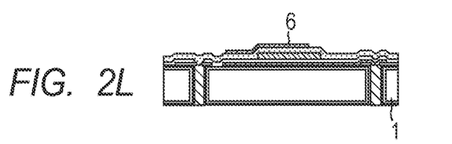

Then, as illustrated in FIG. 2L, the second electrode 6 is formed. The second electrode 6 is formed as part of the vibration film 9 so as to be opposed to the first electrode 4, and the second electrode 6 is one of electrodes for driving the vibration film 9 (see FIG. 2O). The second electrode 6 may have a configuration similar to the configuration of the first electrode 4, and may be formed in a manner similar to the manner of the first electrode 4. Moreover, the second electrode 6 is electrically conductively formed for each cell in the same element.

Figure 2M:
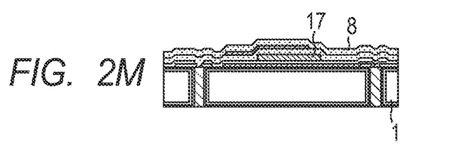

Then, as illustrated in FIG. 2M, the insulating film 8 is formed. The insulating film 8 spreads in contact with the entire upper surface of the second electrode 6, and one of roles thereof is to serve as an insulating protective film for the second electrode 6. It is desirable that the insulating film 8 be formed at a temperature of 400° C. or lower. The insulating film 8 may have a configuration similar to the configuration of the insulating film 7, and may be formed in a manner similar to the manner of the insulating film 7.

Figure 2N:
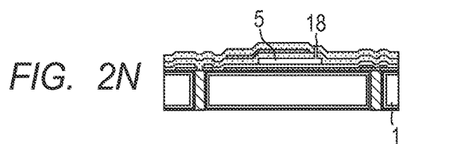

Then, as illustrated in FIG. 2N, an etching hole 18 is formed, and the sacrifice layer 17 (see FIG. 2M) is removed. The etching hole 18 is an opening that passes through the insulating films 7 and 8 and serves to etch the sacrifice layer 17. As a method of forming the etching hole 18, a method including etching mask formation including photolithography, and dry etching including reactive ion etching or wet etching using chemicals can be used. The sacrifice layer 17 is removed using etching liquid or etching gas through the etching hole 18. As a result of the removal of the sacrifice layer 17, the gap 5 is formed.

Figure 2O:
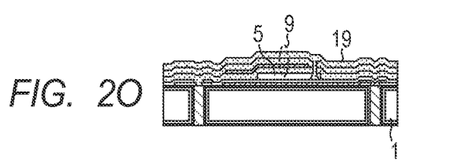

Then, as illustrated in FIG. 2O, a thin film 19 is formed. The thin film 19 seals the etching hole 18, and forms the vibration film 9 that can vibrate above the gap 5, together with the insulating film 7, the second electrode 6 and the insulating film 8. The material and the thickness etc. of the thin film 19 are determined so as to favorably seal the etching hole 18 and suit the performance of the vibration film 9. It is desirable that the thin film 19 be formed at a temperature of 400° C. or lower. The thin film 19, which is an insulating film, may have a configuration similar to the configuration of the insulating film 7, and the thin film 19 may be formed in a manner similar to the manner of the insulating film 7. If needed, the thickness of the thin film 19 is made smaller within a range which the sealing of the etching hole 18 is not influenced, whereby the mechanical performance of the vibration film 9 is adjusted.

It is desirable that the vibration film 9 including the insulating film 7, the second electrode 6, the insulating film 8 and the thin film 19 have a tensile stress of 1 GPa or less. In the case where the vibration film 9 has a compressive stress, one of sticking and buckling may occur in the vibration film 9, so that the vibration film 9 may significantly deform. The sticking, in this case, means that the vibration film 9 as a structure sticks to the insulating film 16 on the substrate side after the removal of the sacrifice layer 17. On the other hand, in the case where the vibration film 9 has a high tensile stress, the vibration film 9 is likely to break. The material, the film thickness, film formation conditions and heat treatment conditions after the film formation of each of the insulating film 7, the second electrode 6, the insulating film 8 and the thin film 19 are designed such that the vibration film 9 has a tensile stress of 1 GPa or less.

Figure 2P:
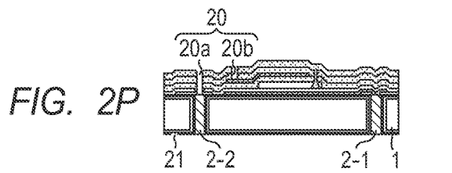
Figure 2Q:
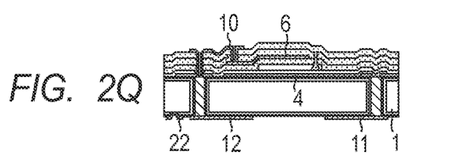

Then, as illustrated in FIG. 2P, contact holes 20 (including 20a and 20b) are formed on the first surface 1a side of the substrate 1 (see FIG. 2A), and a contact hole 21 is formed on the second surface 1b side of the substrate 1 (see FIG. 2A). At least part of the outer circumference of the contact hole 20a is located on the inner side of the opening of the holding member 3. More desirably, the contact hole 20a is completely located on the inner side of the opening of the holding member 3. As a method of forming the contact holes 20 and 21, a method including etching mask formation including photolithography, and dry etching including reactive ion etching or wet etching using chemicals can be used.

Then, as illustrated in FIG. 2Q, the connection wiring 10 is formed on the first surface 1a side of the substrate 1, and the electrode pads 11, 12 and 22 are formed on the second surface 1b side of the substrate 1. The connection wiring 10 connects the second electrode 6 to the through wiring 2-2

(see FIG. 2F) through the contact holes 20a and 20b (see FIG. 2P). The electrode pad 11 connected to the through wiring 2-1 (see FIG. 2F) and the electrode pad 12 connected to the through wiring 2-2 (see FIG. 2F) are formed on the second surface 1b side of the substrate 1. Moreover, the electrode pad 22 that is connected to the substrate 1 through the contact hole 21 (see FIG. 2P) is formed on the second surface 1b side of the substrate 1. Because at least part of the outer circumference of the contact hole 20a is located on the inner side of the opening of the holding member 3, even if film deformation occurs near the opening of the holding member 3, the second electrode 6 and the leading end of the through wiring 2-2 can be reliably connected to each other. The methods of forming the connection wiring 10 and the electrode pads 11, 12 and 22 may be, for example, similar to the method of forming the first electrode 4.

In the present embodiment, as illustrated in FIG. 2G, the first electrode 4 and the through wiring 2-1 are connected to each other by forming the portion 4a of the first electrode 4 directly on the leading end of the through wiring 2-1. Alternatively, the first electrode 4 and the through wiring 2-1 can also be connected to each other similarly to the connection between the second electrode 6 and the through wiring 2-2 using the contact holes 20 and the connection wiring 10.

For the purpose of improving close adhesiveness between films, insulation properties, and preventing interdiffusion, the above-mentioned manufacturing method includes respectively providing films having such effects and functions between adjacent films. Moreover, for the purpose of improving close adhesiveness between films, it is effective to apply surface treatment on each underlying film before forming a next film thereon. The surface of the underlying film is cleaned or activated by the surface treatment. For examples, as a surface treatment, plasma treatment or treatment using liquid can be used.

Then, although not illustrated, the capacitive transducer is connected to the control circuit with the intermediation of the electrode pads 11, 12 and 22. As a method for this connection, direct connection of metal parts, connection using bumps, connection using an ACF and wire bonding can be used. When the capacitive transducer is driven, bias voltage is applied to the first electrode 4, and the second electrode 6 is used as a signal application electrode or a signal take-out electrode. Alternatively, the opposite may be adopted. In needed, the substrate 1 is grounded through the electrode pad 22 to reduce signal noise.

As described above, according to the method of manufacturing the capacitive transducer of the present embodiment, the leading end of each through wiring is held by the holding member on the substrate surface on which the vibration film is formed. Accordingly, such effects as described in the first embodiment can be produced.

Hereinafter, more specific examples are described.

Example 1

With reference to FIG. 1A and FIG. 1B, a basic configuration example of a capacitive transducer of Example 1 is described. The capacitive transducer of the present example has such a configuration as illustrated in FIG. 1A.

The substrate 1 is made of insulating glass having both surfaces that are mirror-polished, and the surface roughness Ra thereof is less than 5 nm. The thickness of the substrate 1 is 180 μm. Each through wiring 2 has a columnar structure containing Cu as a main material thereof. The leading ends of the through wiring 2 are respectively exposed on the first surface 1a and the second surface 1b of the substrate 1, and the diameter of the outer circumference 2b of the leading ends are about 30 μm.

The holding member 3 is formed so as to hold the leading end of the through wiring 2 on the first surface 1a side of the substrate 1. As illustrated in FIG. 1A and FIG. 1B, the holding member 3 has a circular plate shape, the diameter of the inner circumference 3a is about 20 μm, the diameter of the outer circumference 3b is about 50 μm, and the holding member 3 is substantially concentric with the leading end of the through wiring 2. In the region between the outer circumference 3b and the outer circumference 2b, the holding member 3 closely adheres to the first surface 1a of the substrate 1. In the region between the outer circumference 2b and the inner circumference 3a, the holding member 3 holds part of the leading end of the through wiring 2. In the region on the inner side of the inner circumference 3a, the holding member 3 has the opening having a diameter of about 20 μm, and the part 2a of the leading end of the through wiring 2 is exposed.

The first electrode 4 is formed on the first surface 1a side of the substrate 1, and covers an entire region below the gap 5. Moreover, the first electrode 4 is connected to the through wiring 2-1 that is one of the through wirings 2, and the first electrode 4 is further connected to the electrode pad 11 formed on the second surface 1b side of the substrate 1 through the through wiring 2-1. The first electrode 4 is formed by laminating a Ti film having a thickness of 5 nm and an aluminum alloy (an alloy obtained by mixing small amounts of Si and Cu with Al as a main component) film having a thickness of 200 nm in order on the first surface 1a of the substrate 1. A main role of the Ti film is to improve close adhesiveness of the first electrode 4 to the first surface 1a of the substrate 1.

The second electrode 6 is provided on the first surface 1a side of the substrate 1 with the gap 5 from the first electrode 4. For electrical insulation, the second electrode 6 is formed so as to be sandwiched between the insulating films 7 and 8. The second electrode 6 is connected to the through wiring 2-2 that is one of the through wirings 2 by the wiring electrode 10, and the through wiring 2-2 is further connected to the electrode pad 12 formed on the second surface 1b side of the substrate 1 through the through wiring 2-2. The portion of the wiring electrode 10 connected to the leading end of the through wiring 2-2 is located completely on the inner side of the opening of the holding member 3, and reliably connects the second electrode 6 to the leading end of the through wiring 2-2. The second electrode 6 is formed by laminating a Ti film having a thickness of 5 nm, an aluminum alloy (an alloy obtained by mixing small amounts of Si and Cu with Al as a main component) film having a thickness of 200 nm and a Ti film of 5 nm in order. A main role of the Ti film is to: improve close adhesiveness of the second electrode 6 to the insulating films 7 and 8; and prevent interdiffusion.

The gap 5 has a columnar structure having a diameter of about 30 μm and a height of 150 nm. The insulating films 7 and 8 function as insulating protective films for the second electrode 6, and they form the vibration film 9 of the cell together with the second electrode 6. The insulating films 7 and 8 are each made of silicon nitride. The thickness of the insulating film 7 is 200 μm, and the thickness of the insulating film 8 is 400 μm. The vibration film 9 including the insulating film 7, the second electrode 6 and the insulating film 8 has a tensile stress of 0.7 GPa or less. This is achieved by adjusting film formation conditions of the insulating film 7, the second electrode 6 and the insulating film 8 and heat treatment conditions after the film formation.

The wiring electrode 10 is formed by laminating a Ti film having a thickness of 5 nm and an aluminum alloy (an alloy obtained by mixing small amounts of Si and Cu with Al as a main component) film having a thickness of 200 nm in order. A main role of the Ti film is to: improve close adhesiveness of the wiring electrode 10 to the insulating films 7 and 8; and prevent interdiffusion. The electrode pads 11 and 12 are each formed by laminating a Cr film having a thickness of 5 nm and an Al film having a thickness of 200 nm in order. A main role of the Cr film is to provide the electrode pads 11 and 12 with favorable close adhesiveness to the second surface 1b of the substrate 1 and the leading ends the through wirings 2 (including 2-1 and 2-2).

Although not illustrated, the capacitive transducer is connected to the control circuit using an ACF with the intermediation of the electrode pads 11 and 12. When the capacitive transducer is driven, bias voltage is applied to the first electrode 4, and the second electrode 6 is used as a signal application electrode or a signal take-out electrode.

Also in the present example, such effects as described in the first embodiment can be produced.

Example 2

With reference to FIG. 2A to FIG. 2Q, an example method of manufacturing a capacitive transducer of Example is described. First, as illustrated in FIG. 2A, the substrate 1 having the first surface 1a and the second surface 1b is prepared. The substrate 1 is made of low-resistance silicon having both surfaces that are mirror-polished, surface roughness Ra thereof is less than 2 nm, and the resistivity thereof is 0.01 Ω·cm. The thickness of the substrate 1 is 200 μm.

Then, as illustrated in FIG. 2B, the through holes 13 are formed penetrating the substrate 1 from the first surface 1a to the second surface 1b are formed. Each through hole 13 has a substantially columnar shape, and the diameter of the opening thereof on each of the first surface 1a and the second surface 1b of the substrate 1 is about 20 μm. The through hole 13 is formed using the deep RIE technique of silicon. After the deep RIE, the inner wall 13a of the through hole 13 is smoothed by repeating thermal oxidation of the silicon and removal of the resultant thermally oxidized film several times. Then, as illustrated in FIG. 2C, the insulating film 14 is formed on the surface of the substrate 1 including the first surface 1a, the second surface 1b and the inner wall 13a of each through hole 13 (see FIG. 2B). The insulating film 14 is made of silicon oxide having a thickness of about 1 μm, and is formed by thermal oxidation of silicon.

Then, as illustrated in FIG. 2D, the insulating film 15 is further formed on the surface of the insulating film 14. One of roles of the insulating film 15 is to serve as a barrier layer for preventing the material of the through wirings 2 to be formed in FIG. 2E from diffusing to the insulating film 14. The insulating film 15 is made of silicon nitride having a thickness of about 100 nm, and is formed using low pressure CVD (LP-CVD).

Then, as illustrated in FIG. 2E, the through wirings 2 that penetrate the substrate 1 from the first surface 1a to the second surface 1b are respectively formed in the through holes 13. Each through wiring 2 contains Cu as a main material thereof, and substantially fills the inside of the through hole 13. The through wiring 2 is formed using electrolytic plating and a polishing technique. Specifically, first, electrolytic plating of Cu is performed with the second surface 1b of the substrate 1 closely adhering to a substrate with a seed layer (not illustrated). After the plating, the substrate with the seed layer is removed. Then, CMP is performed on the first surface 1a and the second surface 1b of the substrate 1, whereby the first surface 1a and the second surface 1b are planarized. When the CMP is performed on Cu, the insulating film 15 made of silicon nitride serves as a stopper layer for the CMP on Cu. After the CMP on Cu, CMP is performed on the insulating film 15. After the CMP, the surface roughness Ra of the first surface 1a of the substrate 1 becomes less than 5 nm. Moreover, the leading ends of the through wiring 2 are respectively concaved by about 0.5 μm at the maximum with respect to the first surface 1a and the second surface 1b of the substrate 1.

Then, as illustrated in FIG. 2F, the holding member 3 that holds the leading end of each through wiring 2 is formed on the first surface 1a side of the substrate 1. As illustrated in FIG. 2F and FIG. 1B, the holding member 3 is a circular plate whose inner circumference 3a has a diameter of about 12 μm and whose outer circumference 3b has a diameter of about 30 μm, and is substantially concentric with the leading end of the through wiring 2. In the region between the outer circumference 3b and the outer circumference 2b, the holding member 3 closely adheres to the first surface 1a of the substrate 1 with the intermediation of the insulating films 14 and 15. In the region between the outer circumference 2b and the inner circumference 3a, the holding member 3 holds part of the leading end of the through wiring 2. In the region on the inner side of the inner circumference 3a, the part 2a (having a diameter of about 12 μm) of the leading end of the through wiring 2 is exposed. The holding member 3 is made of silicon oxide having a thickness of about 1 μm. The film of the silicon oxide is formed using sputtering at a substrate temperature of 50° C. or lower. The pattern of the holding member 3 is formed using a method including photolithography and reactive ion etching.

Then, as illustrated in FIG. 2G, the first electrode 4 is formed on the first surface 1a side of the substrate 1. The first electrode 4 is one of electrodes for driving the vibration film. The first electrode 4 covers the entire region below the gap 5, and includes: the portion located below the vibrating portion of the vibration film 9; and the portion 4a connected to the through wiring 2-1 that is one of the through wirings 2. The first electrode 4 is electrically conductively formed for each cell in the same element. The first electrode 4 is formed by laminating a Ti film having a thickness of 5 nm and an aluminum alloy film having a thickness of 200 nm in order. A main role of the Ti film is to secure close adhesiveness of the first electrode 4 to an underlying film. The first electrode 4 is formed using a method including formation of a metal film by sputtering, photolithography and dry etching of the metal film.

Then, as illustrated in FIG. 2H, the insulating film 16 is formed. The insulating film 16 covers the surface of the first electrode 4, and one of roles thereof is to serve as an insulating protective film for the first electrode 4. The insulating film 16 is a film of silicon oxide having a thickness of 200 nm, and is formed using CVD at a substrate temperature of about 300° C.

Then, as illustrated in FIG. 2I, the sacrifice layer 17 is formed. The sacrifice layer 17 serves to define the gap 5 of the cell, and is made of Cr. First, a Cr film is formed using electron beam evaporation. Then, the Cr film is processed into a desired shape using a method including photolithography and wet etching. The sacrifice layer 17 is formed so as to have a columnar structure having a diameter of about 30 μm and a height of 150 nm.

Then, as illustrated in FIG. 2J, the hole 16a is formed. The hole 16a is an opening of the insulating film 16, and the opening serves to connect the second electrode 6 to the through wiring 2-2 that is one of the through wirings 2. The hole 16a has a circular shape having a diameter of about 15 µm, and is substantially concentric with the opening 3a of the holding member 3.

Then, as illustrated in FIG. 2K, the insulating film 7 is formed. The insulating film 7 spreads in contact with the entire lower surface of the second electrode 6 to be formed in FIG. 2L, and one of roles thereof is to serve as an insulating protective film for the second electrode 6. The insulating film 7 is made of silicon nitride having a thickness of 200 nm. The film of the silicon nitride is formed using plasma enhanced CVD (PE-CVD) at a substrate temperature of about 300° C. During the film formation, the flow rate of film formation gas is controlled such that the film of the silicon nitride as the insulating film 7 has a tensile stress of about 0.1 GPa.

Then, as illustrated in FIG. 2L, the second electrode 6 is formed. The second electrode 6 is formed above the vibration film so as to be opposed to the first electrode 4, and the second electrode 6 is one of electrodes for driving the vibration film 9. The second electrode 6 has a configuration similar to the configuration of the first electrode 4, and is formed in a manner similar to the manner of the first electrode 4. Moreover, the second electrode 6 is electrically conductively formed for each cell in the same element. Film formation conditions of the second electrode 6 are adjusted such that the second electrode 6 has a tensile stress of 0.4 GPa or less when the manufacture of the capacitive transducer is completed.

Then, as illustrated in FIG. 2M, the insulating film 8 is formed. The insulating film 8 spreads in contact with the entire upper surface of the second electrode 6, and one of roles thereof is to serve as an insulating protective film for the second electrode 6. The insulating film 8 has a configuration similar to the configuration of the insulating film 7, and is formed in a manner similar to the manner of the insulating film 7.

Then, as illustrated in FIG. 2N, the etching hole 18 is formed, and the sacrifice layer 17 is removed. First, the etching hole 18 is formed using a method including photolithography and reactive ion etching. Then, the sacrifice layer 17 is removed by introducing etching liquid through the etching hole 18. As a result, the gap 5 having the same shape as the shape of the sacrifice layer 17 is formed.

Then, as illustrated in FIG. 2O, the thin film 19 is formed. The thin film 19 seals the etching hole 18, and forms the vibration film 9 that can vibrate above the gap 5, together with the insulating film 7, the second electrode 6 and the insulating film 8. The thin film 19 is made of silicon nitride having a thickness of 300 nm. The thin film 19 is formed using PE-CVD at a substrate temperature of about 300° C., similarly to the insulating film 7. The thin film 19 has a tensile stress of about 0.1 GPa. The vibration film 9 formed in this way has a tensile stress of about 0.7 GPa as a whole. Hence, sticking and buckling do not occur in the vibration film 9, and the vibration film 9 is less likely to break.

Then, as illustrated in FIG. 2P, the contact holes 20 (including 20a and 20b) are formed on the first surface 1a side of the substrate 1, and the contact hole 21 is formed on the second surface 1b side of the substrate 1. The contact hole 20a has a columnar shape having a diameter of about 10 µm, and the outer circumference thereof is located on the inner side of the opening 3a of the holding member 3. The contact holes 20 (including 20a and 20b) and the contact hole 21 are formed using a method including photolithography and reactive ion etching.

Then, as illustrated in FIG. 2Q, the connection wiring 10 and the electrode pads 11, 12 and 22 are formed respectively. The connection wiring 10 is formed on the first surface 1a side of the substrate 1. The connection wiring 10 connects the second electrode 6 to the through wiring 2-2 that is one of the through wirings 2, through the contact holes 20a and 20b. Because the outer circumference of the contact hole 20a is located on the inner side of the opening of the holding member 3, even if film deformation occurs near the opening of the holding member 3, the second electrode 6 and the leading end of the through wiring 2-2 are reliably connected to each other by the connection wiring 10. The electrode pad 11 connected to the through wiring 2-1 and the electrode pad 12 connected to the through wiring 2-2 are formed on the second surface 1b side of the substrate 1. Moreover, the electrode pad 22 that is connected to the substrate 1 through the contact hole 21 is formed on the second surface 1b side of the substrate 1. The connection wiring 10 and the electrode pads 11, 12 and 22 have the same configuration as the configuration of the first electrode 4, and are formed in the same manner as the manner of the first electrode 4.

For the purpose of improving close adhesiveness between the insulating films 7, 8 and 19, the above-mentioned manufacturing method includes applying plasma treatment on the surface of each underlying film before forming a next film thereon. The surface of the underlying film is cleaned or activated by the plasma treatment. Then, although not illustrated, the capacitive transducer is connected to the control circuit using an ACF with the intermediation of the electrode pads 11, 12 and 22. When the capacitive transducer is driven, bias voltage is applied to the first electrode 4, and the second electrode 6 is used as one of a signal application electrode or a signal take-out electrode. The substrate 1 is grounded through the electrode pad 22 to reduce signal noise.

As described above, according to the method of manufacturing the capacitive transducer of the present example, the leading end of each through wiring is held by the holding member on the substrate surface on which the vibration film is formed. Accordingly, such effects as described in the first embodiment can be produced.

Example 3

Figure 3A:
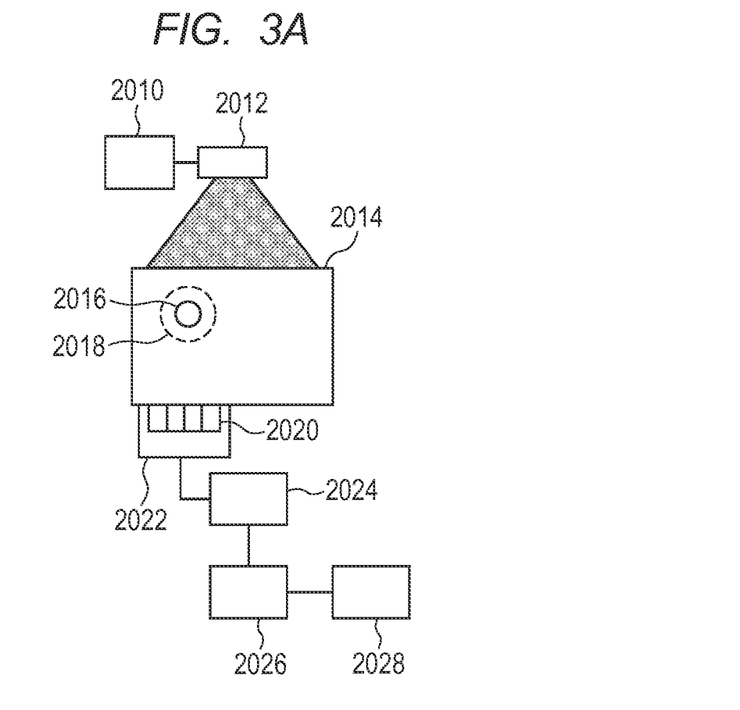
FIG. 3A and FIG. 3B are diagrams for describing an example information acquiring apparatus including the capacitive transducer according to the present invention.

FIG. 3A illustrates an example subject information acquiring apparatus using a photoacoustic effect. Pulsed light emitted from a light source 2010 passes through an optical member 2012 such as a lens, a mirror and an optical fiber, and a subject 2014 is irradiated with the pulsed light. A light absorber 2016 provided inside of the subject 2014 absorbs energy of the pulsed light, and generates photoacoustic waves 2018 that are acoustic waves. A capacitive transducer 2020 of the present invention provided inside of a probe 2022 receives the photoacoustic waves 2018, and the capacitive transducer 2020 converts the photoacoustic waves 2018 into electric signals. Then the capacitive transducer 2020 outputs the electric signals to a signal processing unit 2024. The signal processing unit 2024 performs signal processing such as A/D conversion and amplification on the received electric signals, and outputs the processed signals to a data processing unit 2026. The data processing unit 2026 acquires subject information (characteristic information in which optical characteristic values of the subject, such as a light absorption coefficient, are reflected) as image data using the received signals. Here, the signal processing unit 2024 and the data processing unit 2026 are collectively referred to as processing unit. A display unit 2028 displays an image based on the image data received from the data processing unit 2026. As described above, the subject information acquiring apparatus of the present example includes: the capacitive transducer of the present invention; the light source; and the data processing unit. Then, the transducer receives the photoacoustic waves generated by irradiating the subject with the light emitted from the light source, and converts the received waves into the electric signals. The data processing unit acquires the subject information using the electric signals.

Figure 3B:
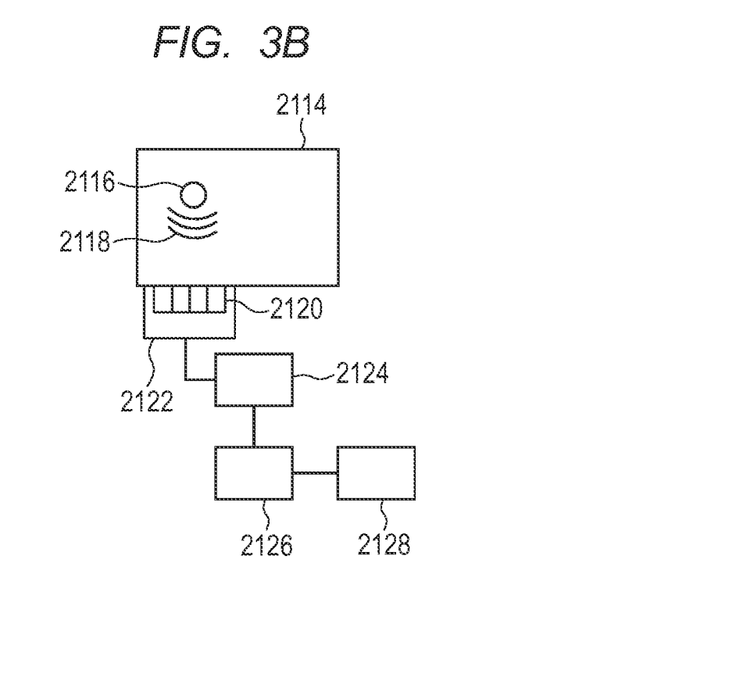

FIG. 3B illustrates an example subject information acquiring apparatus such as an ultrasonographic diagnostic apparatus using reflection of acoustic waves. A capacitive transducer 2120 of the present invention provided inside of a probe 2122 transmits acoustic waves to a subject 2114, and the acoustic waves are reflected on a reflector 2116. The transducer 2120 receives the reflected acoustic waves (reflected waves) 2118, and the capacitive transducer 2120 converts the reflected waves 2118 into electric signals. Then the capacitive transducer 2120 outputs the electric signals to a signal processing unit 2124. The signal processing unit 2124 performs signal processing such as A/D conversion and amplification on the received electric signals, and outputs the processed signals to a data processing unit 2126. The data processing unit 2126 acquires subject information (characteristic information in which a difference in acoustic impedance is reflected) as image data using the received signals. Also in this example, the signal processing unit 2124 and the data processing unit 2126 are collectively referred to as processing unit. A display unit 2128 displays an image based on the image data received from the data processing unit 2126. As described above, the subject information acquiring apparatus of the present example includes: the capacitive transducer of the present invention; and the processing unit that acquires the subject information using the electric signals received from the transducer. The transducer receives the acoustic waves from the subject, and outputs the electric signals.

Note that the probe may be a probe that mechanically moved for scanning or a probe that are moved by a user such as a doctor and an operator with respect to the subject (handheld type). Moreover, in the case of the apparatus using the reflected waves as illustrated in FIG. 3B, a probe for transmitting acoustic waves may be provided separately from a probe for receiving acoustic waves. Further, both the functions of the apparatuses of FIG. 3A and FIG. 3B may be provided to one apparatus, and both the subject information in which optical characteristic values of the subject are reflected and the subject information in which a difference in acoustic impedance is reflected may be acquired. In this case, the transducer 2020 of FIG. 3A may be capable of not only performing the photoacoustic wave reception but also both the acoustic wave transmission and the reflected wave reception.

In the capacitive transducer of the present invention, the leading end of each through wiring is held by the holding member, on the substrate surface side on which the vibration film is formed. Accordingly, even in a temperature rising state during manufacture, the end part of the through wiring is suppressed from protruding from the substrate surface on the vibration film side.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-273672, filed Dec. 28, 2013, which is hereby incorporated by reference herein in its entirety.

What is claimed is:

1. A method of manufacturing a capacitive transducer that comprises a plurality of cells with each cell comprising a first electrode and a vibration film on a first surface side of a substrate having a through wiring that penetrates the substrate from a first surface to a second surface of the substrate, the vibration film including a second electrode that is formed with a gap from the first electrode, the method comprising:
    forming a holding member that holds a leading end of the through wiring, on the first surface side of the substrate having the through wiring; and
    forming the cell after the forming of the holding member.

2. The method of manufacturing the capacitive transducer according to claim 1, wherein the forming of the holding member includes forming the holding member such that the holding member has an opening for exposing part of the leading end of the through wiring.

3. The method of manufacturing the capacitive transducer according to claim 1, wherein the forming of the cell comprises:
    forming the first electrode on the first surface side of the substrate;
    forming a sacrifice layer on the first electrode;
    forming the second electrode on the sacrifice layer; and
    etching the sacrifice layer.

4. The method of manufacturing the capacitive transducer according to claim 3, wherein the forming of the first electrode is such that the first electrode is electrically connected to the through wiring.

5. The method of manufacturing the capacitive transducer according to claim 3, wherein the forming of the second electrode is such that the second electrode is electrically connected to the through wiring.

6. A capacitive transducer comprising:
    a plurality of cells with each cell comprising a first electrode and a vibration film on a first surface side of a substrate having a through wiring that penetrates the substrate from a first surface to a second surface of the substrate, the vibration film including a second electrode that is formed with a gap from the first electrode,
    wherein a holding member that holds a leading end of the through wiring is provided on the first surface side of the substrate.

7. The capacitive transducer according to claim 6, wherein a yield stress of the holding member in a length direction of the through wiring is equal to or more than 1.7 times a shear strength of the through wiring.

8. The capacitive transducer according to claim 6, wherein the holding member has a thermal expansion coefficient closer to the thermal expansion coefficient of the substrate than the thermal expansion coefficient of the through wiring.

9. The capacitive transducer according to claim 6, wherein:
    the holding member is made of a silicon compound, and
    the through wiring is made of a material containing a metal.

10. The capacitive transducer according to claim 6, wherein part of the leading end of the through wiring and the first electrode are connected to each other in an opening of the holding member.

11. The capacitive transducer according to claim 6, wherein part of the leading end of the through wiring and the second electrode are connected to each other in an opening of the holding member.

12. A subject information acquiring apparatus comprising:
the capacitive transducer according to claim 6; and
a processing unit that acquires information of a subject using an electric signal received from the transducer, wherein
the transducer receives an acoustic wave from the subject, and converts the acoustic wave into the electric signal.

13. The subject information acquiring apparatus according to claim 12, further comprising a light source, wherein:
the transducer receives a photoacoustic wave generated by irradiating the subject with light emitted from the light source, and converts the received wave into an electric signal, and
the processing unit acquires the information of the subject using the electric signal.

14. A device comprising:
a substrate;
a through wiring that penetrates the substrate from a first surface to a second surface of the substrate;
an electrode provided on or over the first surface of the substrate and connected to the through wiring; and
a holding member holding a leading end of the through wiring provided on a side of the first surface of the substrate.

15. The device according to claim 14, wherein the holding member is a plate having an opening, and
wherein the electrode and the leading end of the through wiring are electrically connected via the opening.

16. The device according to claim 15, wherein the plate comprises an inner circumference part corresponding to the opening, and an outer circumference part.

17. The device according to claim 16, wherein the through wiring comprises a circular outer circumference part.

18. The device according to claim 17, wherein the plate is substantially concentric with the circular outer circumference part of the through wiring.

19. The device according to claim 18, wherein in a region between the outer circumference part of the plate and the circular outer circumference part of the through wiring, the plate closely adheres to the first surface of the substrate.

20. The device according to claim 14, wherein a material of the holding member contains an oxide or a nitride.

21. The device according to claim 20, wherein the material is silicon oxide, silicon nitride, titanium oxide, yttrium oxide, or aluminum oxide.

22. The device according to claim 14, wherein a thickness of the holding member is 0.1 µm to 2 µm.

23. The device according to claim 14, wherein a cross-sectional shape of the through wiring is substantially circular, and a diameter thereof is 20 µm to 100 µm.

* * * * *